United States Patent
Lee et al.

(10) Patent No.: US 6,699,951 B2
(45) Date of Patent: Mar. 2, 2004

(54) MONOMER AND POLYMER FOR PHOTORESIST, PHOTORESIST COMPOSITION, AND PHOSPHOR LAYER COMPOSITION FOR COLOR CATHODE RAY TUBE

(75) Inventors: Beom-Wook Lee, Uiwang (KR); Ik-Chul Lim, Suwon (KR); Seung-Joon Yoo, Suwon (KR)

(73) Assignee: Samsung SDI Co., Ltd., Suwon (KR)

( * ) Notice: Subject to any disclaimer, the term of this patent is extended or adjusted under 35 U.S.C. 154(b) by 0 days.

(21) Appl. No.: 10/076,317

(22) Filed: Feb. 14, 2002

(65) Prior Publication Data

US 2002/0143130 A1 Oct. 3, 2002

(30) Foreign Application Priority Data

Apr. 3, 2001 (KR) ........................ 2001-17600

(51) Int. Cl.$^7$ ............................................. C08F 124/00
(52) U.S. Cl. .................... 526/266; 526/270; 526/317.1; 526/320; 526/332; 430/270.1
(58) Field of Search ................. 526/266, 270, 526/317.1; 430/320, 332, 270.1

(56) References Cited

U.S. PATENT DOCUMENTS

| | | | |
|---|---|---|---|
| 3,558,310 A | 1/1971 | Mayaud | 96/36.1 |
| 3,808,004 A | 4/1974 | Thomas et al. | 96/68 |
| 3,884,703 A | 5/1975 | Oba et al. | 96/115 R |
| 3,917,794 A | 11/1975 | Akagi et al. | 427/68 |
| 3,933,499 A | 1/1976 | Traskos | 96/68 |
| 3,965,278 A | 6/1976 | Duinker et al. | 427/54 |
| 4,086,090 A | 4/1978 | Kohashi et al. | 96/35.1 |
| 4,093,465 A | 6/1978 | Chu et al. | 96/115 R |
| 4,099,937 A | 7/1978 | Ufken et al. | 55/212 |
| 4,123,276 A | 10/1978 | Kita et al. | 96/91 R |
| 4,154,614 A | 5/1979 | Tsunoda et al. | 96/75 |
| 4,172,729 A | 10/1979 | Naritomi et al. | 96/75 |
| 4,191,571 A | 3/1980 | Nonogaki et al. | 430/335 |
| 4,241,162 A | 12/1980 | Hatano et al. | 430/28 |
| 4,254,197 A | 3/1981 | Miura et al. | 430/28 |
| 4,296,193 A | 10/1981 | Moriya et al. | 430/149 |
| 4,332,874 A | 6/1982 | Hayashi et al. | 430/28 |
| 4,471,043 A | 9/1984 | van de Vorle | 430/159 |
| 4,477,552 A | 10/1984 | Day et al. | 430/175 |
| 4,511,640 A | 4/1985 | Liu | 430/157 |
| 4,539,285 A | 9/1985 | Duyal et al. | 430/157 |
| 4,556,626 A | 12/1985 | Speigel | 430/274 |
| 4,588,669 A | 5/1986 | Asano | 430/156 |
| 4,596,755 A | 6/1986 | Koike et al. | 430/196 |
| 4,614,701 A | 9/1986 | Mori et al. | 430/175 |
| 4,618,562 A | 10/1986 | Walls et al. | 430/157 |
| 4,645,730 A | 2/1987 | Fromson et al. | 430/155 |
| 4,650,738 A | 3/1987 | Platzer et al. | 430/143 |
| 4,731,316 A | 3/1988 | Tomiyasu et al. | 430/157 |
| 4,745,042 A | 5/1988 | Sasago et al. | 430/156 |
| 4,902,602 A | 2/1990 | Misu et al. | 430/175 |

(List continued on next page.)

FOREIGN PATENT DOCUMENTS

| | | |
|---|---|---|
| JP | 50-38459 | 8/1973 |
| JP | 55-24126 | 2/1980 |
| JP | 57-182379 | 11/1982 |
| JP | 60-247238 | 12/1985 |
| JP | 62-145626 | 6/1987 |
| JP | 5-173331 | 7/1993 |
| JP | 05-216219 | 8/1993 |
| KR | 1999-12415 | 3/2000 |
| KR | 1999-12416 | 3/2000 |
| KR | 1999-15235 | 3/2000 |
| KR | 2000-37354 | 7/2000 |
| KR | 1999-58898 | 10/2000 |

OTHER PUBLICATIONS

Lin et al. Journal of Materials Science (1992), 27(11), 2902–7.*

* cited by examiner

Primary Examiner—Helen L. Pezzuto
(74) Attorney, Agent, or Firm—Christie, Parker & Hale, LLP

(57) ABSTRACT

Disclosed are a monomer, a polymer for a photoresist, a photoresist composition and a phosphor layer for a cathode ray tube. The polymer has the formula 1:

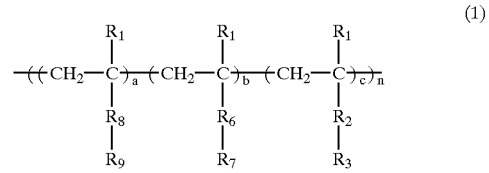

wherein: $R_1$ is H or $CH_3$, $R_2$ is $(R)_\alpha(CH_2)_\beta R'$ or $(R)_\alpha((CH_2)_mO)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5,

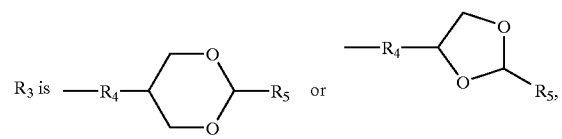

$R_4$, which combines an acetal compound and a vinyl compound, is a saturated or unsaturated $C_1$–$C_5$ alkyl, a $C_1$–$C_5$ ether, or a $C_1$–$C_5$ carbonyl; $R_5$ is a saturated or unsaturated $C_1$–$C_5$ alkyl, a $C_1$–$C_5$ ether, or a $C_1$–$C_5$ carbonyl; $R_6$ and $R_8$ are identical or are each independently a single bond, $(R)_\alpha(CH_2)_\beta R'$ or $(R)_\alpha((CH_2)_mO)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5; $R_7$ is a hydroxyl group; $R_9$ is a carboxyl group; a, b, and c each represent the mole ratio of its corresponding monomer, wherein a and b each have a value of 0 to 0.99, and c has a value of 0.01 to 0.3; and n represents the degree of polymerization of each polymer and has a value of at least 2.

9 Claims, No Drawings

U.S. PATENT DOCUMENTS

| | | |
|---|---|---|
| 4,954,418 A | 9/1990 | Koike ........................ 430/175 |
| 4,960,671 A | 10/1990 | Dickinson ................... 430/175 |
| 4,990,417 A | 2/1991 | Inada et al. ................... 430/28 |
| 5,024,920 A | 6/1991 | Morishita et al. ........... 430/325 |
| 5,053,310 A | 10/1991 | Platzer ....................... 430/162 |
| 5,059,698 A | * 10/1991 | Schulthess et al. ......... 549/375 |
| 5,173,382 A | 12/1992 | Morishita et al. ............. 430/28 |
| 5,260,161 A | 11/1993 | Matsumura et al. ........ 430/161 |
| 5,272,036 A | 12/1993 | Tani et al. .................. 430/191 |
| 5,385,804 A | 1/1995 | Premlatha et al. .......... 430/195 |
| 5,424,165 A | 6/1995 | Sekiya ....................... 430/157 |
| 5,506,089 A | 4/1996 | Gybin et al. ................ 430/287 |

MONOMER AND POLYMER FOR PHOTORESIST, PHOTORESIST COMPOSITION, AND PHOSPHOR LAYER COMPOSITION FOR COLOR CATHODE RAY TUBE

CROSS REFERENCE TO RELATED APPLICATION

This application is based on application No. 2001-17600 filed in the Korean Industrial Property Office on Apr. 3, 2001, the disclosure of which is incorporated herein by reference.

1. Field of the Invention

The present invention relates to a monomer and a polymer for a photoresist, a photoresist composition, and a phosphor layer composition for a color cathode ray tube. More particularly, the present invention relates to a photoresist composition for a color cathode ray tube which causes no environmental pollution and has good storage stability and high sensitivity.

2. Background of the Invention

As electro beams emitted from an electron gun hit phosphor on a phosphor layer, the energy of the electron beams is converted into photon energy to excite the phosphor.

The phosphor layer is generally made through the following process. An inner surface of a panel with a black matrix is coated with a phosphor slurry and dried. The coated panel is exposed to a high-pressure mercury lamp through a photo mask and developed using distilled water. Such a process is repeated three times for green, blue, and red phosphors.

The phosphor slurry includes a phosphor, a photoresist resin which is a photosensitive polymer, additives such as photo-crosslinking agents, agents for increasing adhesion, and dispersion-aids. Alternatively, an additional photoresist composition including a photoresist resin and a photo-crosslinking agent is coated before coating the slurry to improve adhesion of the phosphor.

The photoresist resin and the photo-crosslinking agent may be generally polyvinyl alcohol-sodium dichromate (PVA-SDC) or ammonium dichromate (ADC). Alternatively, they may be a modified polyvinyl alcohol or polyvinyl alcohol introduced with polyvinyl pyrrolidone (U.S. Pat. Nos. 3,558,310 and 4,556,626, and Japanese Patent Laid-open No. Hei. 5-173331). Polyvinyl alcohol-sodium dichromate (PVA-SDC) and ammonium dichromate (ADC) have excellent sensitivity, produce a phosphor pattern without residue in unexposed region. However, it is difficult to control the pattern width. Moreover, their dark erosion reaction causes storage problems, and chrome included in sodium dichromate and ammonium dichromate causes environmental pollution.

Thus, various proposals to use a water-soluble photoresist for printing without chrome in the phosphor slurry for the color cathode ray tube have been attempted. The water-soluble photoresist may be a water-soluble polymer-bisazide or a water-soluble polymer-diazo, or a polyvinyl alcohol-stillbazolium-based compound.

The water-soluble polymer-bisazide-based compound is disclosed in U.S. Pat. Nos. 3,884,703, 3,917,794, 4,086,090, 4,099,937, 4,191,571, 4,254,197, 4,332,874, 4,596,755, and 4,954,418, Japanese Patent Laid-open No. Sho. 57-182379, and Korean Patent Laid-open No. 1999-58898. The water-soluble polymer-diazo-based compound is disclosed in U.S. Pat. Nos. 3,808,004, 3,933,499, 3,965,278, 4,093,465, 4,123,276, 4,154,614, 4,172,729, 4,296,193, 4,471,043, 4,477,552, 4,511,640, 4,539,285, 4,614,701, 4,618,562, 4,645,730, 4,650,738, 4,731,316, 4,745,042, 4,902,602, 4,960,671, 5,053,310, 5,173,382, 5,260,161, 5,272,036, and 55,424,165, Japanese Patent Laid-open Nos. Sho. 50-38459, Sho. 52-3276, Sho. 60-247238, and Sho. 62-145626, and Korean Patent Laid-open Nos. 1999-12415, 1999-12416, and 1999-85157. Polyvinyl alcohol-stillbazolium-based compound is disclosed in U.S. Pat. No. 4,990,417, 5,506, 089, Japanese Patent No. Sho. 55-24126, and Korean Patent Laid-open No.1999-15235.

Water-soluble polymers include polyvinyl alcohol, polyvinyl pyrrolidone, and polyacrylamide (PAD). Photo-crosslinking agents for bisazide compounds include 4,4'-diazidobenzalacetophenone-2-sulfonate, 4,4'-diazidoestillben-2,2'-disulfonate, and 4,4'-diazidostillben-γ-carboxylic acid, and those for diazo compounds include salts of vinylazidobenzylideneacetophenonesulfonic acid, vinylazidobenzylideneacetophenone carboxylic acid, vinylazidocinnamylideneacetophenonesulfonic acid, and vinylazidocinnamyllideneacetophenoecarboxylic acid.

The produced phosphor prepared using the above-described photoresist slurry without chrome has good photosensitivity, good storage stability, but inferior sensitivity and poor adhesion to a panel, when compared with that using a polyvinyl alcohol-sodium dichromate slurry.

Azide polymers exhibiting improved characteristics over the water-soluble polymer-bisazide-based photoresist are disclosed in U.S. Pat. Nos. 4,241,162, 4,588,669, 5,024,920, and 5,385,804, Japanese Patent Laid-open No. Hei. 05-216219, and Korean Patent Laid-open No. 2000-37354. The azide polymer is prepared by binding an azide group into a water-soluble polymer.

The azide polymer has improved sensitivity and degrees of crosslinkage over a mixture of a polymer and an azide compound so that the azide polymer exhibits good adhesion. However, with this process, it is difficult to produce wanted products and it is difficult to introduce azide groups into the polymer at a desired ratio.

SUMMARY OF THE INVENTION

It is an object of the present invention to provide a monomer for a photoresist for a color cathode ray tube without using an environmental pollution causing material.

It is another object to provide a polymer for a photoresist for a cathode ray tube with the monomer.

It is still another object to provide a photoresist composition for a color cathode ray tube, which causes no environmental pollution, good storage stability and high photosensitivity.

It is still another object to provide a phosphor layer composition for a cathode ray tube including the polymer.

These and other objects may be achieved by a monomer for producing photoresist used in a cathode ray tube, presented by formula 2.

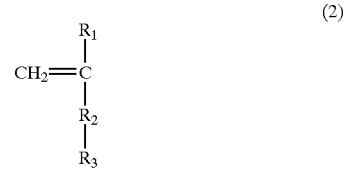
(2)

wherein:

$R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, α is 0 or 1, β is 0 to 5, m is 1 or 2, and γ is 1 to 5, $R_3$ is 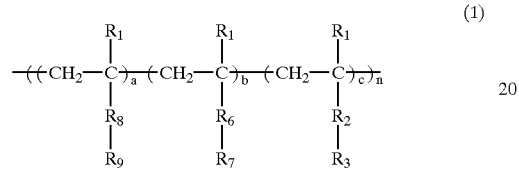 or $R_4$, which combines an acetal compound and a vinyl compound, is a saturated or unsaturated $C_1$–$C_5$ alkyl, a $C_1$–$C_5$ ether, or a $C_1$–$C_5$ carbonyl; and $R_5$ is a saturated or unsaturated $C_1$–$C_5$ alkyl, a $C_1$–$C_5$ ether, or a $C_1$–$C_5$ carbonyl.

The present invention further provides a photoresist polymer for a color cathode ray tube including a monomer of formula 2. Preferred is a polymer of formula 1.

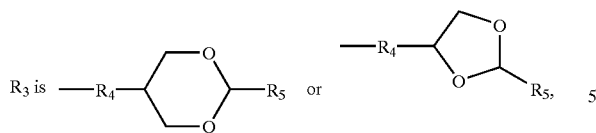

(1)

wherein, $R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is 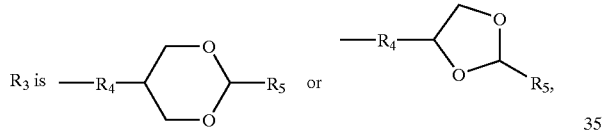 or $R_4$, which combines an acetal compound and a vinyl compound, is a saturated or unsaturated $C_1$–$C_5$ alkyl, a $C_1$–$C_5$ ether, or a $C_1$–$C_5$ carbonyl;

$R_5$ is a saturated or unsaturated $C_1$–$C_5$ alkyl, a $C_1$–$C_5$ ether or a $C_1$–$C_5$ carbonyl;

$R_6$ and $R_8$ are identical or are each independently selected from a single bond, $(R)_\alpha(CH_2)_\beta R'$ and $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5;

$R_7$ is a hydroxyl group;

$R_9$ is a carboxyl group;

a, b, and c each represent the mole ratio of its corresponding monomer, where a and b each have a value of 0 to 0.99, and c has a value of 0.01 to 0.3; and n represents the degree of polymerization of each polymer and has a value of at least 2.

The present invention provides a photoresist composition for a color cathode ray tube including a copolymer of formula 2 and a photo-acid generator. A mixture of a phosphor and the photoresist composition may be used a phosphor layer composition for a color cathode ray tube.

DETAILED DESCRIPTION OF THE INVENTION

The present invention relates to a novel photoresist polymer and composition for a color cathode ray tube, without using an environmental pollution causing material, good storage ability and high precision. The photoresist polymer of the present invention is an acetal polymer which is usable in a slurry photoresist used in a phosphor layer of a color cathode ray tube. The photoresist polymer is represented by formula 1.

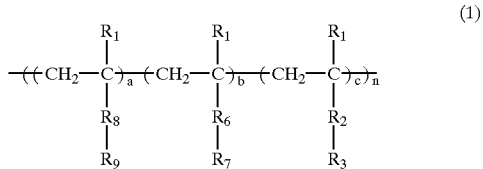

(1)

wherein:

$R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is 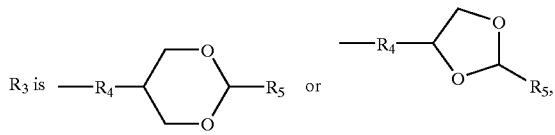 or $R_4$, which combines an acetal compound and a vinyl compound, is a saturated or unsaturated $C_1$–$C_5$ alkyl, a $C_1$–$C_5$ ether, or a $C_1$–$C_5$ carbonyl;

$R_5$ is a saturated or unsaturated $C_1$–$C_5$ alkyl, a $C_1$–$C_5$ ether, or a $C_1$–$C_5$ carbonyl;

$R_6$ and $R_8$ are identical or each independently selected from a single bond, $(R)_\alpha(CH_2)_\beta R'$ and $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5;

$R_7$ is a hydroxyl group;

$R_9$ is a carboxyl group;

a, b, and c each represent mole ratio of its corresponding monomer, where a and b each have a value of 0 to 0.99, and c has a value of 0.01 to 0.3; and n represents the degree of polymerization of each polymer and has a value of at least 2.

The polymer of formula 1 may be prepared by polymerizing a compound of formula 2 with an acetal group, a compound of formula 3 with a hydroxyl group, and a compound of formula 4 with a carboxyl group,

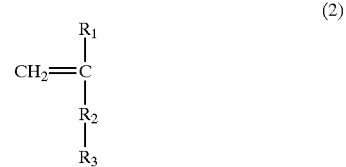

(2)

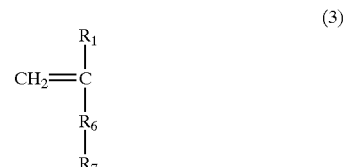

(3)

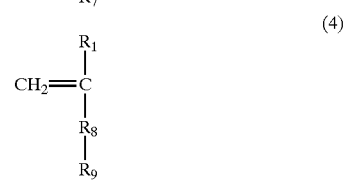

(4)

wherein $R_1$ to $R_3$ and $R_6$ to $R_9$ are the same as defined above.

The compound of formula 2 with an acetal group provides reactive sites which cause a cross-linking reaction through nucleophilic functional groups such as hydroxyl groups or carboxyl groups in the presence of an acid and at an elevated temperature. The compound of formula 3 with a hydroxyl group can improve solubility in water and adhesion between a phosphor layer and a panel, and attack the acetal group to cause a cross-linking reaction. The compound with formula 4 with a carboxyl group can control solubility in water and developing rate, and can attack the acetal group to cause a cross-linking reaction.

The compound of formula 2 with an acetal group is prepared by reacting an alcohol compound with an acetal group and a vinyl compound. The alcohol compound with an acetal group is prepared by reacting an aldehyde and a triol compound.

One example of the preparation will be described in below. The aldehyde and the triol compound are heated together with a constant boiling compound, such as petroleum ether, benzene or toluene, in the presence of an acid, such as paratoluenesulfonic acid, while refluxing. As a result, water is removed from the mixture to prepare a primary alcohol with an acetal group. The primary alcohol reacts with a vinyl compound, such as metacryloyl chloride or acryloyl chloride, in an organic solvent, such as tetrahydrofuran, in the presence of amines, such as triethylamine, to prepare a compound of formula 2 with an acetal group.

The aldehyde may be selected from acetaldehyde, isobutylaldehyde, butylaldehyde, 2-methylbutylaldehyde, 2-ethylbutylaldehyde, valeraldehyde, isovaleraldehyde, 3,3-dimethylbutylaldehyde, 2-methylvaleraldehyde, and 2,3-dimethylvaleraldehyde. The triol compound may be glycerol or 2-(hydroxymethyl)-1,3-propanediol.

The reaction between the alcohol compound with an acetal group and the vinyl compound, and the reaction between the aldehyde and the triol compound are well known and thus the detailed descriptions thereof are omitted.

The polymerization process of the present invention may be a general polymerization process, such as radical polymerization.

The polymer of formula 1 may be prepared by dissolving the monomers of formulas 2 to 4 in an organic solvent, such as tetrahydrofuran or dimethyl sulfoxide, and by reacting the resulting material with an organic-soluble initiator, such as 2,2-azobisisobutylonitrile, benzoyl peroxide or t-butyl peroxide.

The polymer cross-linked in acid is insoluble in a developing solution, and the cross-linking reaction in acid is a chemical amplification reaction. The resulting polymer has high sensitivity.

The cross-linking reaction of a polymer, for example, a polymer with a 6-ring acetal group, according to the present invention will be illustrated in following reaction formula 1. The cross-linking reaction occurs by attacking a nucleophilic functional group, such as a hydroxyl group or carboxyl group, to produce an acetal group in the presence of acid at an elevated temperature. Water participates in the attacking reaction to produce an acetal group. At this time, the acetal group decomposes into a diol and an aldehyde compound, as shown in the reaction formula 2, which results in no cross-linking reaction.

The reaction 1 and the reaction 2 are competitive reactions so that in order to sufficiently complete the cross-linking reaction, reaction 1 should be the predominant reaction. To achieve this result, a layer is formed using a photoresist, and then the amount of water is minimized while the layer properties are maintained. Therefore, the heating temperature is the critical point during the process of forming a phosphor layer.

Reaction formula 1

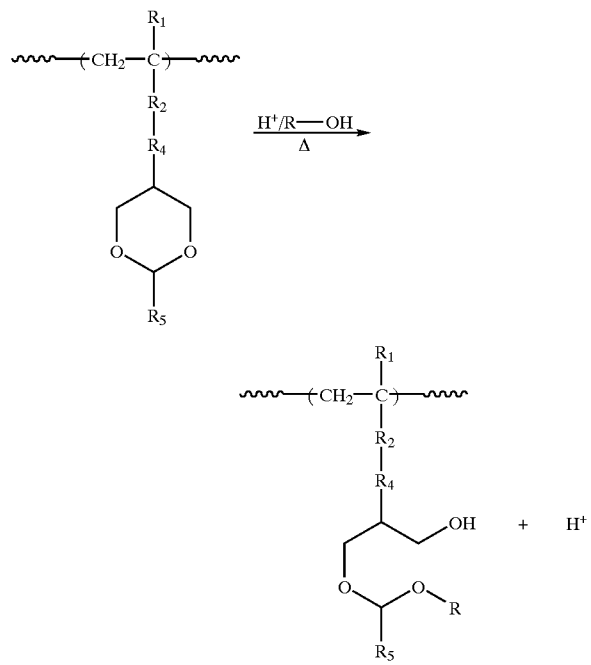

wherein

R-OH is

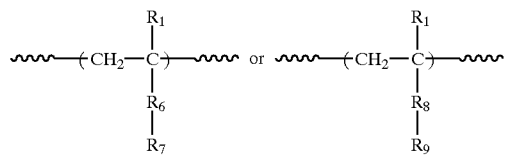

Reaction formula 2

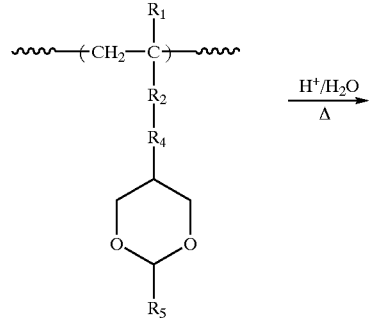

-continued

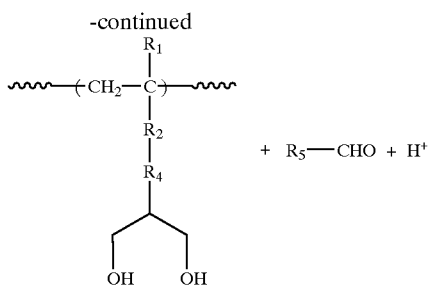

+ R$_5$—CHO + H$^+$

In the reaction formulas 1 and 2, H+ plays the catalyst role in the cross-linking reaction. The generator acid attacks the alcohol group of the polymer to produce an acetal group resulting in a cross-linking reaction. Any compounds that are soluble in water can be used as a photoacid generator. Examples include at least one of a sulfonium or an onium compound, such as diphenyl iodine hexafluorophosphate, diphenyl iodine hexafluoro arsenate, diphenyl iodine hexafluoro antimonite, diphenylparamethoxyphenyl triflate, diphenylparatoluenyl triflate, diphenylparaisobutylphenyl triflate, diphenylpara-t-butylphenyl triflate, triphenylsulfonium hexafluoro phosphate, triphenylsulfonium hexafluoro arsenate, triphenylsulfonium hexafluoro antimonite, triphenylsulfonium triflate, and dibutylnaphtylsulfonium triflate.

The polymer of formula 1 of the present invention may be used in a slurry as well as in a black matrix or an upper in a coating solution. In addition, the polymer of the present invention may be useful for coating or printing.

If the polymer is used as a photoresist for a phosphor layer of a color cathode ray tube, the mole ratio of the acetal group in the polymer of formula 1, providing a cross-linking site, is preferably 0.01 to 0.3. If the mole ratio of the acetal group is less than 0.01, the cross-linking component portion is low so that the cross-linking reaction a does not sufficiently occur and it is difficult to form a phosphor layer. If the mole ratio is more than 0.3, the solubility of the polymer in water is reduced and adhesion between the phosphor layer and a panel is reduced so that it is difficult to form a phosphor layer. The content of the polymer is preferably 2 to 5 wt. % based on the total phosphor slurry and that of the photoacid generator is preferably 0.02 to 0.25 wt. %. If the content of the polymer is less than 2 wt. %, the cross-linking component is low and it is difficult to form a phosphor layer. If the content is more than 5 wt. %, the viscosity increases so that it is difficult to form an even layer. If the content of the photoacid generator is less than 0.02 wt. %, the amount of generated acid is low and the cross-linking reaction does not sufficiently occur. If the content is more than 0.25 wt. %, the photoacid generator absorbs excess ultraviolet rays and sensitivity is reduced.

A method of producing a phosphor layer using the photoresist composition is illustrated in below.

The polymer of the present invention and the photoacid generator are dissolved in water, and green, blue and red phosphors generally used in the color cathode ray tube are added to the resulting material to make a slurry. The slurry is spin-coated on a panel of a color cathode ray tube, formed with black matrix. Alternatively, the slurry composition may include additives such as adhesion-aid or antifoaming agent. The green, blue and red phosphors may be any phosphors generally used in a color cathode ray tube. Exemplary red phosphors are $Y_2O_2S$:Eu and $Y_2O_3$:Eu. An exemplary blue phosphor is ZnS:Ag,Cl. An exemplary green phosphor is ZnS:Au,Cu,Al. The adhesion-increasing agent may be any material that is capable of improving uniformity and dispersion of the slurry. Exemplary thereof are sorbitan mono laulate surfactants (SLS). The antifoaming agent may be any material capable of reducing moisture and surface tension and being improving, and examples thereof are propylene oxide ethylene surfactant (PES) and dinaphthylenedisulfonic acidic soda surfactant (NSS).

The following examples further illustrate the present invention, but the invention is not limited by these examples.

EXAMPLE 1

Preparation of a Vinyl-Based Monomer with an Acetal Group 14.4 g (0.2 mole) of butylaldehyde, 24 g (0.26 mole) of glycerol and 0.3 g of paratoluenesulfonic acid were mixed with 60 g of petroleum ether in a 250 ml flask. The flask was equipped with a dean stark, and the resulting material was refluxed at 90° C. for 6 hours. The reaction was completed, and the reacted material was extracted using water and ether. The extracted material was fractional distilled to obtain 23.1 g (yield 79%) of a pure primary alcohol compound with an acetal group (FW=146.19).

21.9 g (0.15 mole) of the primary alcohol compound and 20 g (0.2 mole) of triethylamine were dissolved in 30 g of purified tetrahydrofuran, and the resulting material was transferred into a 500 ml flask. 18 g (0.17 mole) of metacryloyl chloride was slowly dropped to the flask with a dropping funnel and shaken at room temperature for 6 hours. The amine salt produced during the reaction was removed using a glass filter, and a column chromatography was performed to obtain 20.1 g (yield 67%) of metacrylate monomer of formula 5 with an acetal group (FW=200.23).

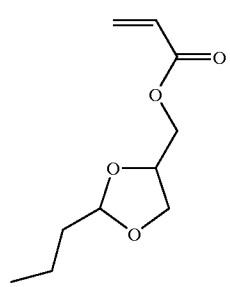

(5)

EXAMPLE 2

14.4 g (0.2 mole) of butylaldehyde, 27.6 g (0.26 mole) of 2-(hydroxymethyl)-1,3-propanediol and 0.3 g of paratoluenesulfonic acid were mixed with 60 g of petroleum ether in a 250 ml flask. The flask was equipped with a dean stark, and the resulting material was refluxed at 90° C. for 6 hours to complete the reaction. The reacted material was extracted using water and ether. The extracted material was fractional distilled to obtain 26 g (yield 81%) of a pure primary alcohol compound with an acetal group (FW=160.21).

24 g (0.15 mole) of the primary alcohol compound and 20 g (0.2 mole) of triethylamine were distilled in 30 g of a purified tetrahydrofuran, and the resulting material was transferred into a 500 ml flask. 18 g (0.17 mole) of acryloyl chlroride was slowly dropped into the flask using a dropping funnel and shaken at room temperature for 6 hours. The amine salt produced during the reaction was removed using a glass filter, and a column choromatography was performed to obtain 20 g (yield 64%) acrylate monomer of formula 6 with an acetal group.

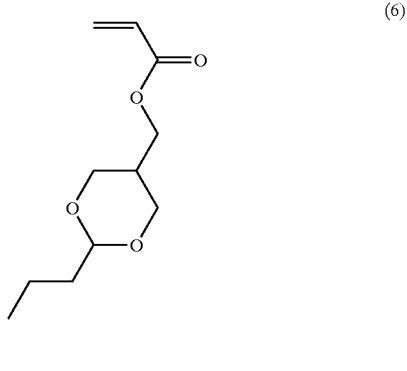

(6)

EXAMPLE 3

The monomer of formula 5 obtained in Example 1 and a 2-hydroxyethylacrylate monomer of formula 3 (wherein $R_1$ is H, $R_6$ is $COOCH_2CH_2$, $R_7$ is OH) were dissolved in a mixed solution of dimethyl sulfoxide and water. The resulting material was transferred into a reacting vessel, and a trace amount of potassium sorbate was added to the vessel in order to prevent gelation. 2,2'-azobisisobutyramide dihydrate as an initiator was added to the obtained material. While nitrogen gas was injected into the vessel, polymerization was performed at 60° C. for 3 hours to obtain a polymer of formula 7,

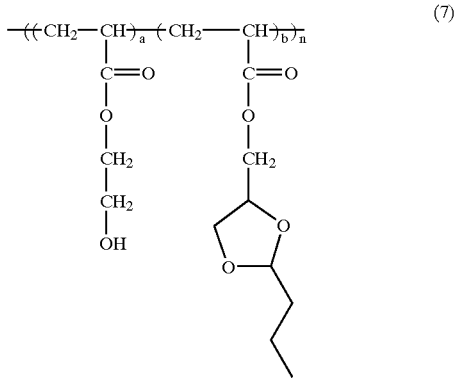

(7)

wherein a=0.97, b=0.03, and n (degree of polymerization)= 7300.

EXAMPLE 4

The monomer of formula 5 obtained in Example 1, a 2-hydroxyethylacrylate monomer of formula 3 (wherein $R_1$ is H and $R_6$ is $COOCH_2CH_2$, $R_7$ is OH), and acrylic acid monomer were dissolved in a mixed solution of dimethyl sulfoxide and water. The resulting material was transferred into a reacting vessel, and a trace amount of potassium sorbate was added to the vessel in order to prevent gelation. 2,2'-azobisisobutyramide dihydrate as an initiator was added to the obtained material. While nitrogen gas was injected into the vessel, polymerization was performed at 60° C. for 3 hours to obtain a polymer of formula 8,

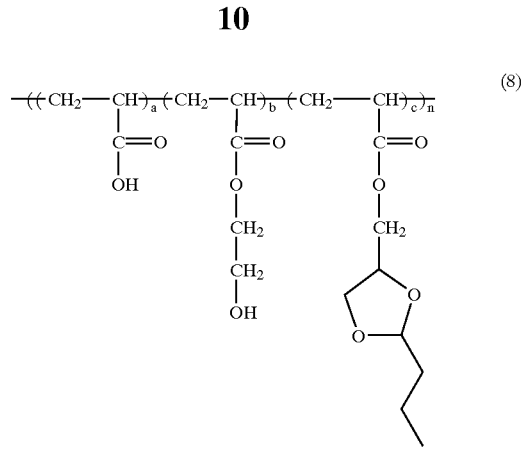

(8)

wherein a=0.17, b=0.78, c-0.05, and n (degree of polymerization)=8800.

EXAMPLE 5

The monomer of formula 6 obtained in Example 2 and a 2-hydroxyethylacrylate monomer of formula 3 (wherein $R_1$ is H and $R_6$ is $COOCH_2CH_2$, $R_7$ is OH) were dissolved in a mixed solution of dimethyl sulfoxide and water. The resulting material was transferred into a reacting vessel, and a trace amount of potassium sorbate was added to the vessel in order to prevent gelation. 2,2'-azobisisobutyramide dihydrate as an initiator was added to the obtained material. While nitrogen gas was injected into the vessel, polymerization was performed at 60° C. for 3 hours to obtain a polymer of formula 9,

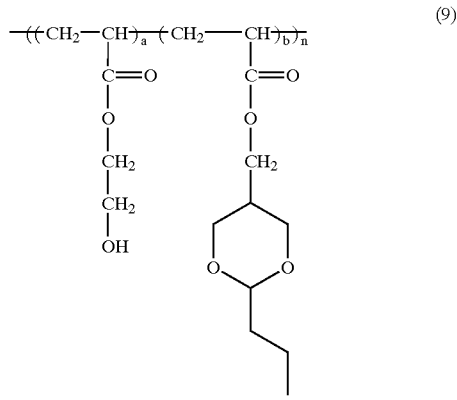

(9)

wherein a=0.97, b=0.03, and n (degree of polymerization)= 6300.

EXAMPLE 6

The monomer of formula 6 obtained in Example 2 and a 2-hydroxyethylacrylate monomer of formula 3 (wherein $R_1$ is H and $R_6$ is $COOCH_2CH_2$, $R_7$ is OH) were dissolved in a mixed solution of dimethyl sulfoxide and water. The resulting material was transferred into a reacting vessel, and a trace amount of potassium sorbate was added to the vessel in order to prevent gelation. 2,2'-azobisisobutyramide dihydrate as an initiator was added to the obtained material. While nitrogen gas was injected into the vessel, polymerization was performed at 60° C. for 3 hours to obtain a polymer of formula 10,

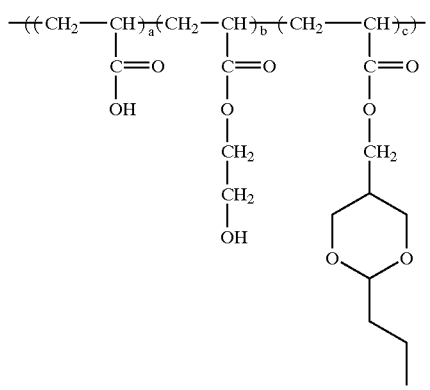

(10)

wherein a=0.13, b=0.83, c=0.04, and n (degree of polymerization)=6100.

APPLICATION EXAMPLE 1

30 g of a polymer having formula 8, 1.5 g of triphenylsulfoniumtriflate, 0.56 g of SLS as an adhesion-increasing agent, 0.56 g of PES as a foaming agent, 350 g of a green phosphor, and 1000 g of pure water were mixed to make a slurry. The slurry was spin-coated on a panel formed with a black matrix, and the coated panel was rotary dried at 90° C. for 2 minutes. The dried panel was exposed to a mercury lamp with high pressure at luminance of 100 mW/cm$^2$ for 16 seconds and heat-treated at 130° C. for 1 minute. The exposed panel was developed using high-pressure pure water at 40° C. for 30 seconds. The developed panel was repeatedly rotary dried at 60° C. for 2 minutes to produce a green phosphor layer with a width of 110 μm.

APPLICATION EXAMPLE 2

A green phosphor layer with a width of 110 μm was produced by the same procedure as Application Example 1, except that 30 g of the polymer having formula 9 obtained in Example 4 was used, and the developing step was performed at a luminance of 100 mW/cm$^2$ for 17 seconds.

APPLICATION EXAMPLE 3

A green phosphor layer with a width of 110 μm was produced by the same procedure as Application Example 1, except that 30 g of the polymer having formula 10 obtained in Example 5 was used, and the developing step was performed at a luminance of 100 mW/cm for 15 seconds.

APPLICATION EXAMPLE 4

A green phosphor layer with a width of 110 μm was produced by the same procedure as Application Example 1, except that 30 g of the polymer having formula 11 obtained in Example 6 was used, and the developing step was performed at a luminance 100 mW/cm $^2$ for 17 seconds.

COMPARATIVE EXAMPLE 1

30 g of polyvinyl alcohol, 3.7 g of sodium dichromate, 0.56 g of SLS as an adhesion-increasing agent, 0.56 g of PES as an antifoaming agent, 350 g of a green phosphor, and 1000 g of pure water were mixed in an experimental room blocked extreme ultraviolet ray to make a slurry. The slurry was spin-coated on a panel formed with black matrix, and the coated panel was rotary dried at 60° C. for 2 minutes. The dried panel was exposed to a mercury lamp with a luminance of 100 mW/cm$^2$ for 30 seconds, and the exposed panel was developed using high-pressure pure water for 30 seconds. The exposed panel was repeatedly dried at 60° C. for 2 minutes to produce a green phosphor layer with a width of 110 μm.

Application Examples 1 to 4 using the polymer of the present invention requires 15 to 17 seconds of exposing time, but Comparative example 1 using PVA-SDC requires 30 seconds of exposing time. Thus, the photoresist of the present invention exhibits better sensitivity than PVA-SDC.

The photoresist composition includes a photoacid generator so that the cross-linking reaction occurs as a chemical amplification type, and a phosphor layer having good sensitivity can be produced. In addition, the photoresist of the present invention contains no environmental pollution-causing materials or heavy metal such as chrome and is environmental friendly.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A polymer for a photoresist for a color cathode ray tube comprising a copolymer, the copolymer being prepared with a monomer having formula 2:

(2)

wherein:
$R_1$ is H or $CH_3$,
$R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, α is 0 or 1, β is 0 to 5, m is 1 or 2, and γ is 1 to 5,
$R_3$ is

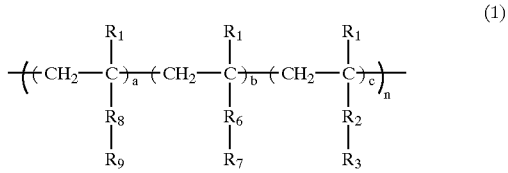

$R_4$, which combines an acetal compound and a vinyl compound, is a saturated or unsaturated $C_1$–$C_5$ alkyl, a $C_1$–$C_5$ ether, and a $C_1$–$C_5$ carbonyl; and
$R_5$ is a saturated or unsaturated $C_1$–$C_5$ alkyl, a $C_1$–$C_5$ ether of, or a $C_1$–$C_5$ carbonyl.

2. A polymer for a photoresist for a color cathode ray tube having the formula 1:

(1)

wherein:
$R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is

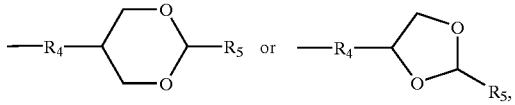

$R_4$, which combines an acetal compound and a vinyl compound, is a saturated or unsaturated $C_1$–$C_5$ alkyl, a $C_1$–$C_5$ ether, or a $C_1$–$C_5$ carbonyl;

$R_5$ is a saturated or unsaturated $C_1$–$C_5$ alkyl, a $C_1$–$C_5$ ether, or a $C_1$–$C_5$ carbonyl;

$R_6$ and $R_8$ are identical or are each independently a single bond, $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5;

$R_7$ is a hydroxyl group;

$R_9$ is a carboxyl group;

a, b, and c each represent the mole ratio of its corresponding monomer, wherein a and b have a value of 0 to 0.99, and c has a value of 0.01 to 0.3; and n represents the degree of polymerization of each polymer and has a value at least 2.

3. The polymer according to claim 2, wherein:

$R_1$ is H, $R_2$ is COO, $R_3$ is

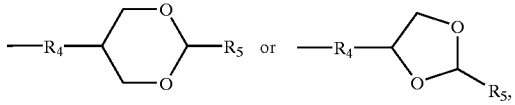

$R_4$ is $CH_2CH_2$, $R_5$ is $CH_2CH_2CH_3$, $R_6$ is $COOCH_2CH_2$, $R_7$ is OH, $R_8$ is a single bond, and $R_9$ is COOH.

4. A photoresist composition for a color cathode ray tube comprising:

a copolymer; and a photoacid generator, the copolymer being prepared with a monomer having formula 2:

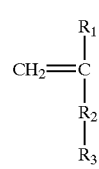
(2)

wherein:

$R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is

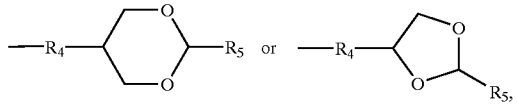

$R_4$, which combines an acetal compound and a vinyl compound, is a saturated or unsaturated $C_1$–$C_5$ alkyl, a $C_1$–$C_5$ ether, or a $C_1$–$C_5$ carbonyl; and $R_5$ is a saturated or unsaturated $C_1$–$C_5$ alkyl, a $C_1$–$C_5$ ether, or a $C_1$–$C_5$ carbonyl.

5. The photoresist composition according to claim 4 wherein the copolymer is a copolymer having formula 1:

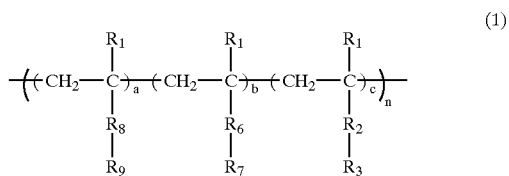
(1)

wherein:

$R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is

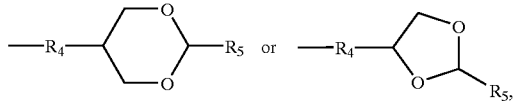

$R_4$, which combines an acetal compound and a vinyl compound, is a saturated or unsaturated $C_1$–$C_5$ alkyl, a $C_1$–$C_5$ ether, or a $C_1$–$C_5$ carbonyl;

$R_5$ is a saturated or unsaturated $C_1$–$C_5$ alkyl, a $C_1$–$C_5$ ether, or a $C_1$–$C_5$ carbonyl;

$R_6$ and $R_8$ are identical or are each independently a single bond, $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5;

$R_7$ is a hydroxyl group;

$R_9$ is a carboxyl group;

a, b, and c each represent the mole ratio of its corresponding monomer, wherein a and b each have a value of 0 to 0.99, and c has a value of 0.01 to 0.3; and n represents the degree of polymerization of each polymer and has a value of at least 2.

6. The polymer composition according to claim 5, wherein:

$R_1$ is H, $R_2$ is COO, $R_3$ is

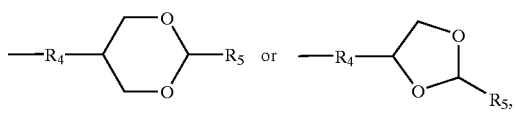

$R_4$ is $CH_2CH_2$, $R_5$ is $CH_2CH_2CH_3$, $R_6$ is $COOCH_2CH_2$, $R_7$ is OH, $R_8$ is a single bond, and $R_9$ is COOH.

7. A phosphor layer composition for a color cathode ray tube comprising:

a copolymer;

a photoacid generator; and a phosphor, the copolymer being prepared with a monomer having formula 2:

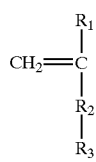 (2)

wherein:

$R_1$ is H or $CH_3$, $R_2$ is $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is

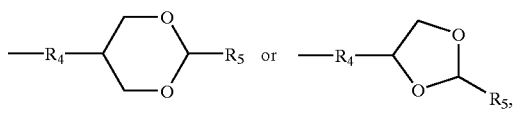

$R_4$, which combines an acetal compound and a vinyl compound, is a saturated or unsaturated $C_1$–$C_5$ alkyl, a $C_1$–$C_5$ ether, or a $C_1$–$C_5$ carbonyl; and $R_5$ is a saturated or unsaturated $C_1$–$C_5$ alkyl, a $C_1$–$C_5$ ether, or a $C_1$–$C_5$ carbonyl.

8. The phosphor layer composition of claim 7 wherein the copolymer has formula 1:

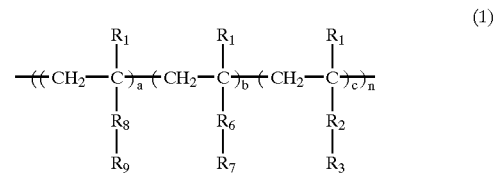 (1)

wherein:

$R_1$ is H or $CH_3$, $R_2$ is $(R)_\alpha(CH_2)_\beta R'$ or $(R)_\beta((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5, $R_3$ is

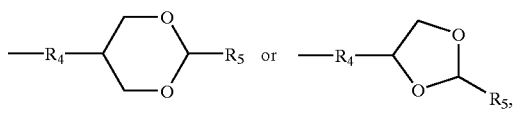

$R_4$, which combines an acetal compound and a vinyl compound, is a saturated or unsaturated $C_1$–$C_5$ alkyl, a $C_1$–$C_5$ ether, or a $C_1$–$C_5$ carbonyl;

$R_5$ is a saturated or unsaturated $C_1$–$C_5$ alkyl, a $C_1$–$C_5$ ether, or a $C_1$–$C_5$ carbonyl;

$R_6$ and $R_8$ are identical or are each independently a single bond, $(R)_\alpha(CH_2)_\beta R'$ or $(R)_\alpha((CH_2)_m O)_\gamma R'$, wherein R is CO, $CO_2$, O, OCO or $OCO_2$, R' is O, $CO_2$, or $OCO_2$, $\alpha$ is 0 or 1, $\beta$ is 0 to 5, m is 1 or 2, and $\gamma$ is 1 to 5;

$R_7$ is a hydroxyl group;

$R_9$ is a carboxyl group;

a, b, and c each represent the mole ratio of its corresponding monomer, wherein a and b each have a value of 0 to 0.99, and c has a value of 0.01 to 0.3; and n represents the degree of polymerization of each polymer and has a value of at least 2.

9. The polymer composition according claim 8, wherein:

$R_1$ is H, $R_2$ is COO, $R_3$ is

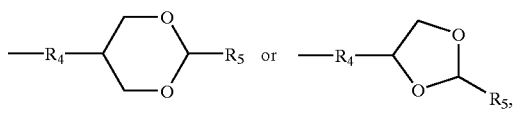

$R_4$ is $CH_2CH_2$, $R_5$ is $CH_2CH_2CH_3$, $R_6$ is $COOCH_2CH_2$, $R_7$ is OH, $R_8$ is a single bond, and $R_9$ is COOH.

* * * * *